(12) United States Patent
Johnson

(10) Patent No.: US 6,471,685 B1
(45) Date of Patent: Oct. 29, 2002

(54) MEDICAL DRESSING ASSEMBLY AND ASSOCIATED METHOD OF USING THE SAME

(76) Inventor: David James Johnson, 3877 MacArthur Rd., Muskegon, MI (US) 49442

(*) Notice: Subject to any disclaimer, the term of this patent is extended or adjusted under 35 U.S.C. 154(b) by 0 days.

(21) Appl. No.: 09/573,749

(22) Filed: May 18, 2000

(51) Int. Cl.$^7$ ................................................. A61K 9/22
(52) U.S. Cl. ..................... 604/890.1; 604/307; 604/180; 602/53; 602/57
(58) Field of Search ............................... 604/890.1, 307, 604/304, 13, 180, 358, 353, 355, 3; 128/888; 606/201, 202; 602/53, 57

(56) References Cited

U.S. PATENT DOCUMENTS

| | | | |
|---|---|---|---|
| 3,875,387 A | * 4/1975 | Barbieri ........................ 602/53 |
| 4,430,013 A | * 2/1984 | Kaufman ........................ 604/3 |
| 5,106,629 A | * 4/1992 | Cartmell et al. ............ 604/304 |
| 5,478,308 A | * 12/1995 | Cartmell et al. .............. 604/13 |
| 5,549,584 A | * 8/1996 | Gross .......................... 604/355 |
| 5,571,080 A | * 11/1996 | Jensen ......................... 604/307 |
| 5,643,236 A | * 7/1997 | Hadley ........................ 604/353 |
| 5,707,348 A | * 1/1998 | Krogh ......................... 604/180 |
| 5,899,871 A | * 5/1999 | Cartmell et al. ............ 604/304 |
| 5,981,822 A | * 11/1999 | Addison ...................... 604/358 |
| 6,191,341 B1 | * 2/2001 | Shippert ...................... 604/304 |

\* cited by examiner

Primary Examiner—Teresa Walberg
Assistant Examiner—Fadi H. Dahbour
(74) Attorney, Agent, or Firm—King & Jovanovic, PLC

(57) ABSTRACT

A medical dressing assembly and associated method of using the same comprising an isolating member, a member for controllably inputting matter and a member for controllably exhausting matter. The isolating member is capable of isolating an affected area of a patient from an external environment. The isolating member includes a patient engaging strap member and a cover member. The patient engaging strap member includes a bottom surface which is positionable so as to be substantially internally facing. The cover member extends away from the patient engaging member. The cover member defines a volume wherein the patient engaging strap member provides access to the volume. The bottom surface of the at least one patient engaging strap member is capable of engaging a portion of the patient, to, in turn, substantially confine at least a portion of the affected area of a patient within the volume defined by the cover member. The member for controllably inputting matter controllably inputs matter into the volume. The member for controllably exhausting matter controllably exhausts matter from the volume.

32 Claims, 11 Drawing Sheets

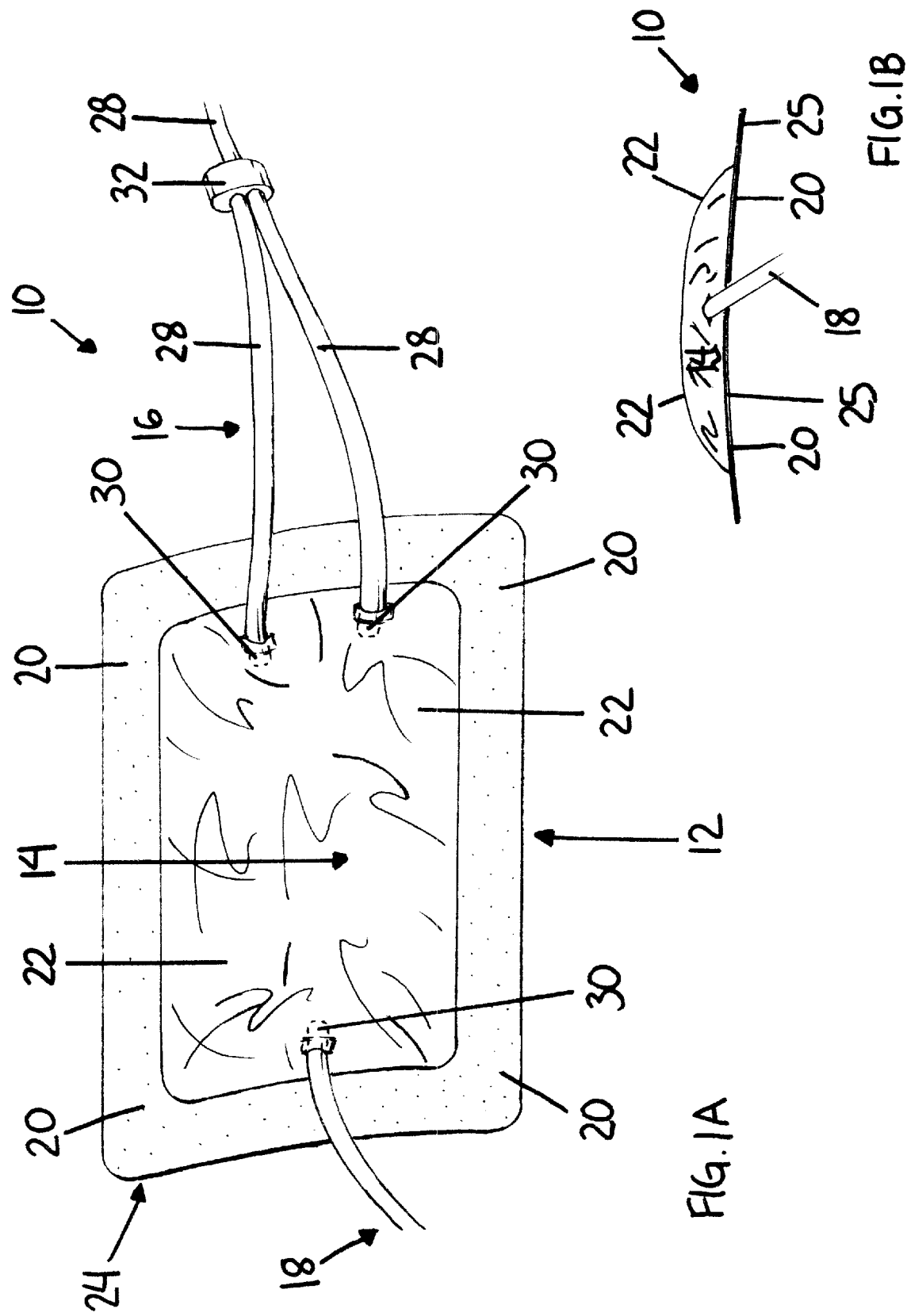

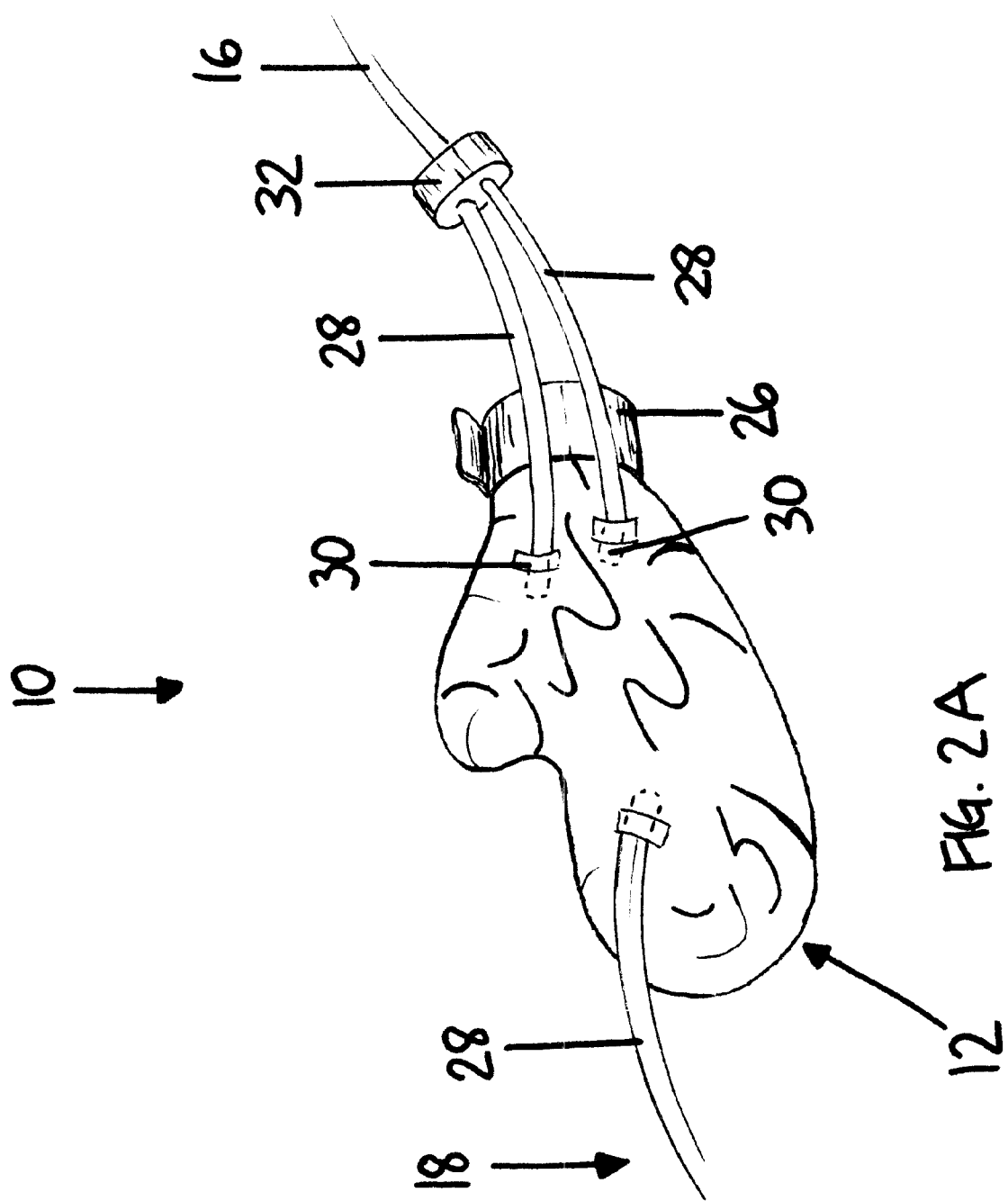

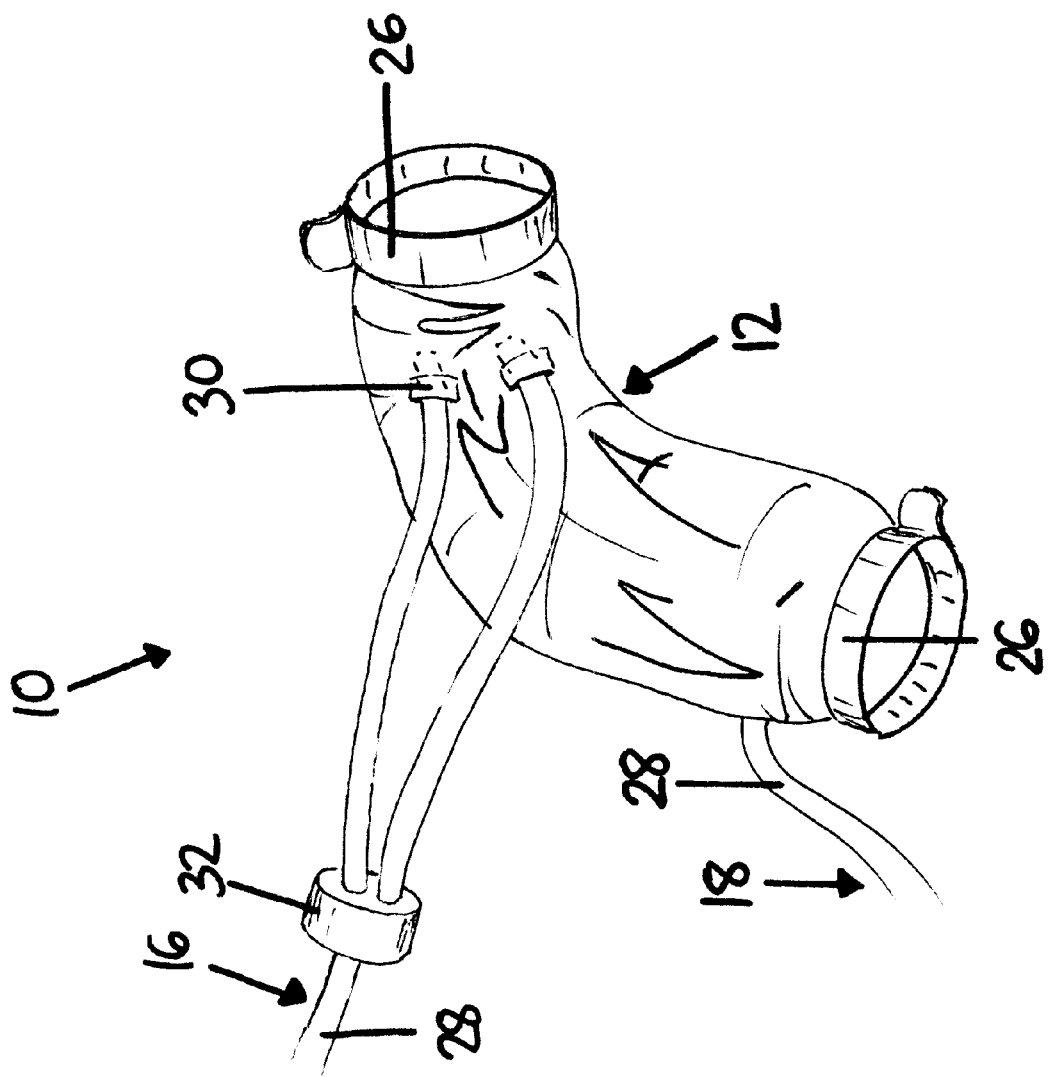

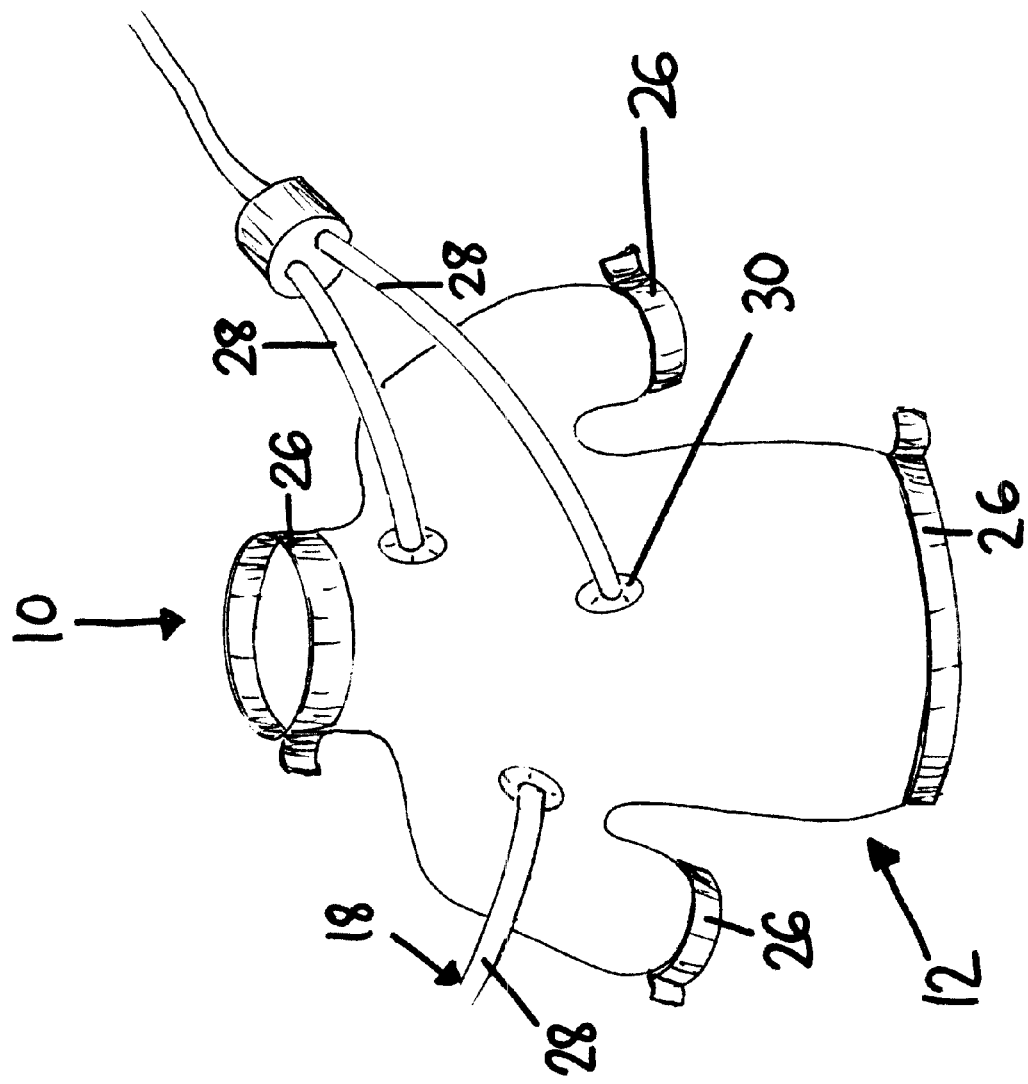

MEDICAL DRESSING ASSEMBLY AND ASSOCIATED METHOD OF USING THE SAME

BACKGROUND OF THE INVENTION

1. Field of the Invention

The present invention relates in general to a medical dressing assembly, and more particularly, to a medical dressing assembly which, among other things, isolates an affected area of a patient, such as a burn, incision, abrasion, and/or other abnormality, without contacting the same. The present invention further relates to an associated method of using such a medical dressing assembly.

2. Background Art

Medical dressings have been known in the art for years. Moreover, treating an affected area of a patient with a medical dressing in cooperation with medication is likewise well known in the art. Indeed, conventionally an affected area of a patient is cleansed, coated with medical ointment, and subsequently wrapped in a bandage or gauze like material, which directly contacts the affected area. In addition, certain types of affected areas require that the patient be given medication internally, such as one or more antibiotics for treating primary and/or secondary bacterial infections, pain killers and/or tranquilizers for treating pain and/or traumatic anxiety. While treating an affected area of a patient using the above-identified conventional medical dressings have become common in today's medical practice, such use remains largely problematic for several reasons.

A first problem associated with a conventional medical dressing is that, the dressing must be removed and a fresh dressing must be reapplied on a regular basis so that discharge from the affected area does not stick or cling to the affected area. Such a process can be time consuming, cumbersome, and extremely painful, especially for burn patients, if the dressing is not removed and fresh dressing reapplied prior to hardening or crusting of the discharged matter.

A second problem recognized with the use of a conventional medical dressing is that the affected area is typically covered with a bandage, thereby substantially precluding air circulation around the affected area. Again, for a burn patient, circulation around the affected area is highly desirous inasmuch as the circulated air provides the patient with substantial relief from the "residual burning" sensation, which often times can be extremely painful and persist for an extended period of time.

A third problem associated with a conventional medical dressing is that it does not substantially preclude fluid from leaving the affected area of the patient. As such, the patient can become dehydrated very rapidly, as a result of the fluid loss, especially if the affected area is large and/or deep. As is well known, dehydration of the patient can lead to many other serious and sometimes fatal complications.

In addition, a conventional medical dressing also substantially precludes continuous topical application of medication to the affected areas inasmuch as the affected area is directly covered and/or wrapped. As such, patients are typically administered large quantities of medicine either orally or intravenously, many of which have adverse side effects, especially at high concentrations. Prolonged administration of powerful drugs at high concentration, such as new generation antibiotics, is not optimal inasmuch as the patient can, over time, develop a resistance to the medication, thereby rendering the medicine less effective, and, at times, completely ineffective. Moreover, due to the concentration requirements of administering medication using conventional means, a patient may not be able to receive a particular medicine if an adverse reaction is observed above a particular concentration.

Furthermore, use of a conventional medical dressing can be problematic when a physician or care taker attempts to observe the affected area for healing or complications because the dressing must be at least partially removed for observation.

Finally, even though a conventional medical dressing covers the affected area of the patient, the affected area is not completely isolated from the external environment, where harmful airborne contaminants and other undesirable matter can inadvertently come into contact with the affected area and further complicate the healing process.

It is therefore an object of the present invention to provide a medical dressing assembly that remedies the aforementioned detriments and/or complications associated with conventional medical dressings.

These and other objects of the present invention will become apparent in light of the present specification, claims, and drawings.

SUMMARY OF THE INVENTION

The present invention is directed to a medical dressing assembly comprising: (a) means for isolating an affected area of a patient from an external environment, wherein placement of the isolation means defines a volume surrounding at least a portion of the affected area of the patient; (b) means for controllably inputting matter into the volume; and (c) means for controllably exhausting matter from the volume.

In a preferred embodiment of the invention, the isolation means is geometrically configurable into at least one of the group consisting of a hand dressing, a forearm dressing, an upper arm dressing, a facial dressing, an upper torso dressing, a lower torso dressing, an upper leg dressing, a lower leg dressing, a foot and ankle dressing, and mixtures thereof.

In another preferred embodiment of the invention, the isolation means comprises: (a) at least one patient engaging member; and (b) a cover member associated with the at least one patient engaging member. In this embodiment the at least one patient engaging member may comprise a patient engaging base member having an inner peripheral geometry greater than the affected area of the patient. Such a patient engaging base member may be at least partially associated with an adhesive, which is preferably covered with a protective, peel-away member. Alternatively, the at least one patient engaging member may comprise a patient engaging strap member, which is optionally adjustable, and may be partially associated with an adhesive, which is preferably covered with a protective, peel-away member.

In yet another preferred embodiment of the invention, the cover member can be non-expandable and/or expandable to define a fixed and/or variable volume, respectively. Preferably the cover member is substantially transparent, thereby enabling observation of the affected area of the patient.

In a preferred embodiment of the invention, the matter inputting means and/or the matter exhausting means includes at least one of a regulator, a clamp, and a filter for controlling the input/output rate of matter into/out of the volume.

The medical dressing assembly may also comprise a source for supplying a controlled gas, such as air, purified air, a noble or inert gas, an oxygen enriched gaseous mixture, oxygen, and mixtures thereof.

In yet another preferred embodiment of the invention, the dressing assembly further comprises one or more of the following: (a) cooling means associated with the matter inputting means; (b) at least one of a vaporizer or a nebulizer associated with the matter inputting means; (c) filtering means associated with the matter exhausting means; and (d) means for collecting discharge matter from the affected area.

It is also contemplated that the medical dressing assembly of the present invention can be pressurizable from approximately ambient pressure to approximately 10 p.s.i.

The present invention is also directed to a medical dressing assembly comprising: (a) an isolating member, capable of isolating an affected area of a patient from an external environment including: (1) at least one patient engaging member; and (2) a cover member associated with the at least one patient engaging member, wherein placement of the isolating member defines a volume surrounding at least a portion of the affected area of the patient; (b) at least one input conduit hermetically associated with the isolation member; and (c) at least one exhaust conduit hermetically associated with the isolation member.

The present invention is further directed to a method of dressing an affected area of a patient comprising the steps of: (a) providing a medical dressing assembly including: (1) an isolating member having at least one patient engaging member and a cover member associated with the isolating member; (2) at least one input conduit; and (3) an exhaust; (b) operatively securing the isolating member associated with the cover member onto the patient so that at least a portion of the affected area of the patient is isolated from an external environment; (c) supplying matter into the medical dressing assembly through the at least one input conduit; and (d) venting matter from the exhaust into an external environment.

BRIEF DESCRIPTION OF THE DRAWINGS

The invention will now be described with reference to the drawings wherein:

FIG. 1A of the drawings is a fragmented perspective view of a medical dressing assembly in accordance with the present invention;

FIG. 1B of the drawings is a side elevational view of a medical dressing assembly in accordance with the present invention;

FIGS. 2A–2I of the drawings are perspective views of various geometrical configurations of medical dressing assemblies fabricated in accordance with the present invention.

DETAILED DESCRIPTION OF THE INVENTION

Figure 2B:
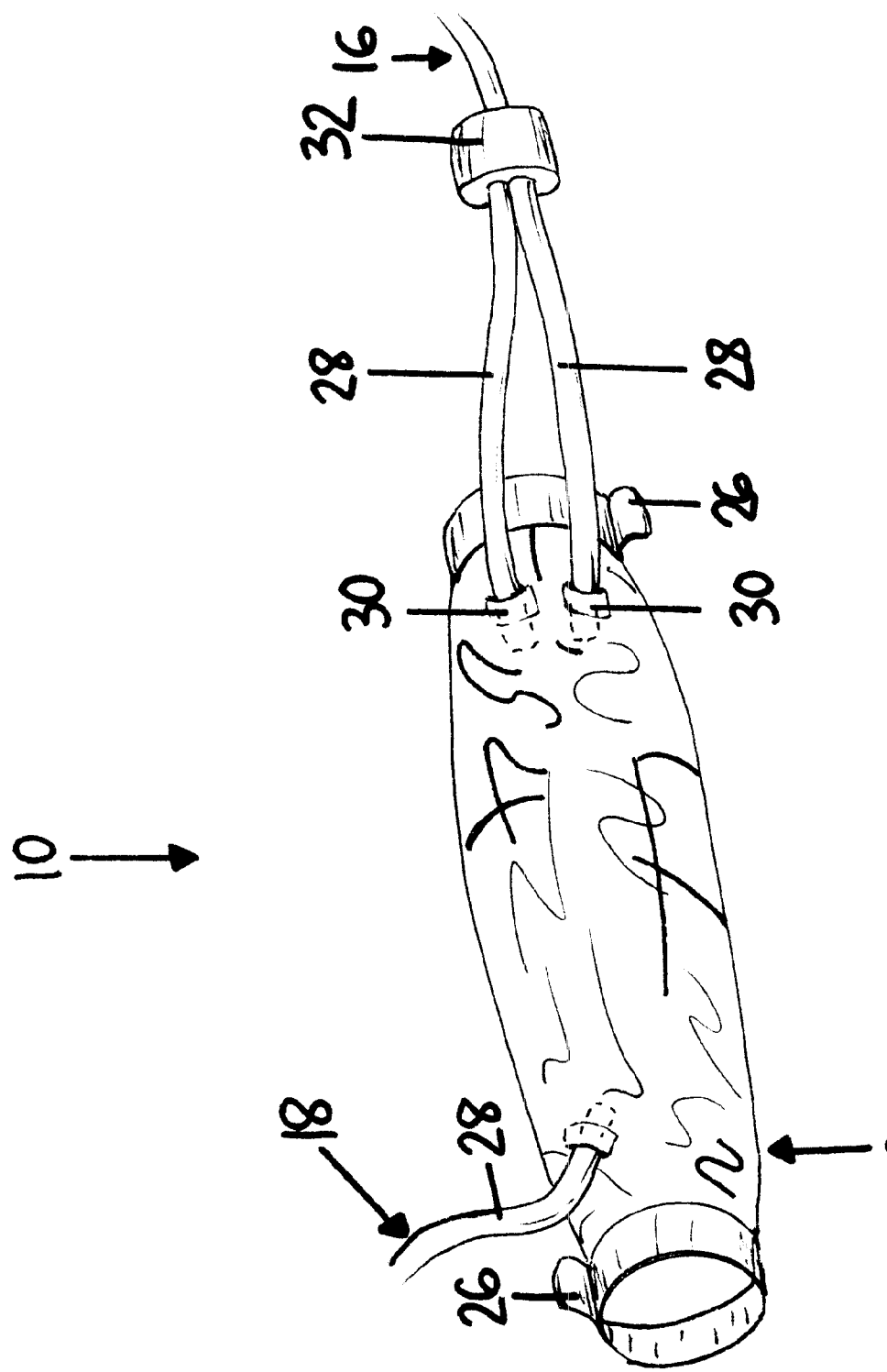
Figure 2D:
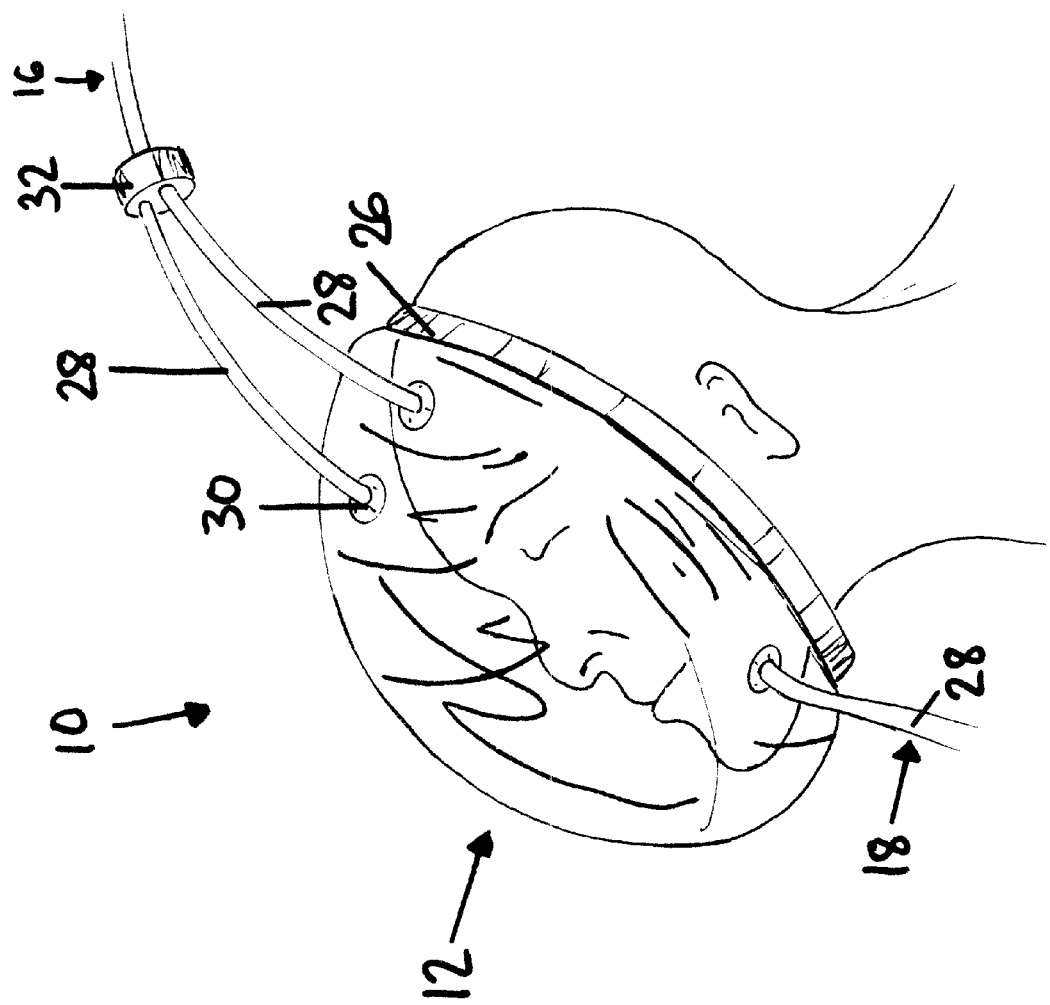
Figure 2F:
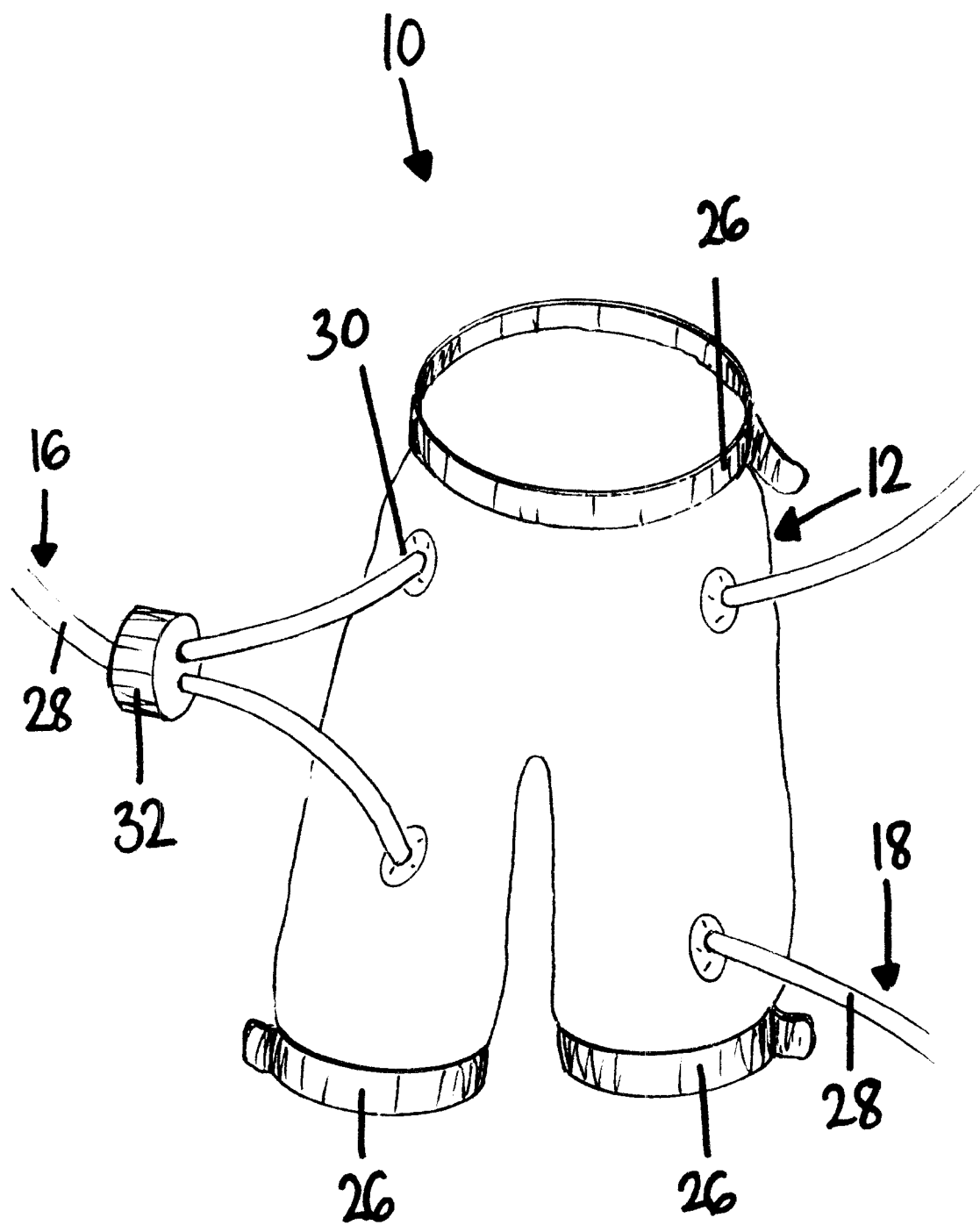
Figure 2G:
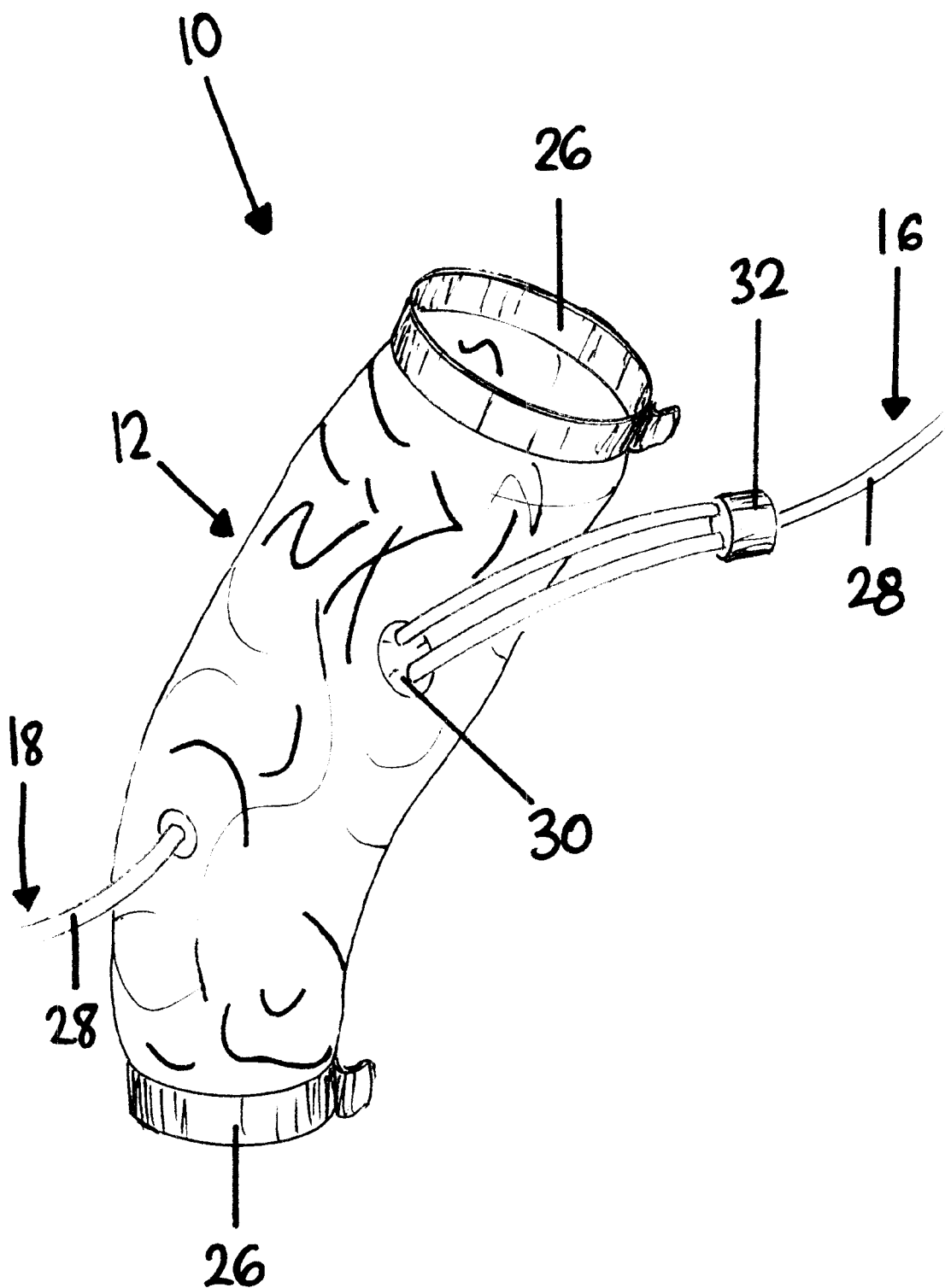
Figure 2H:
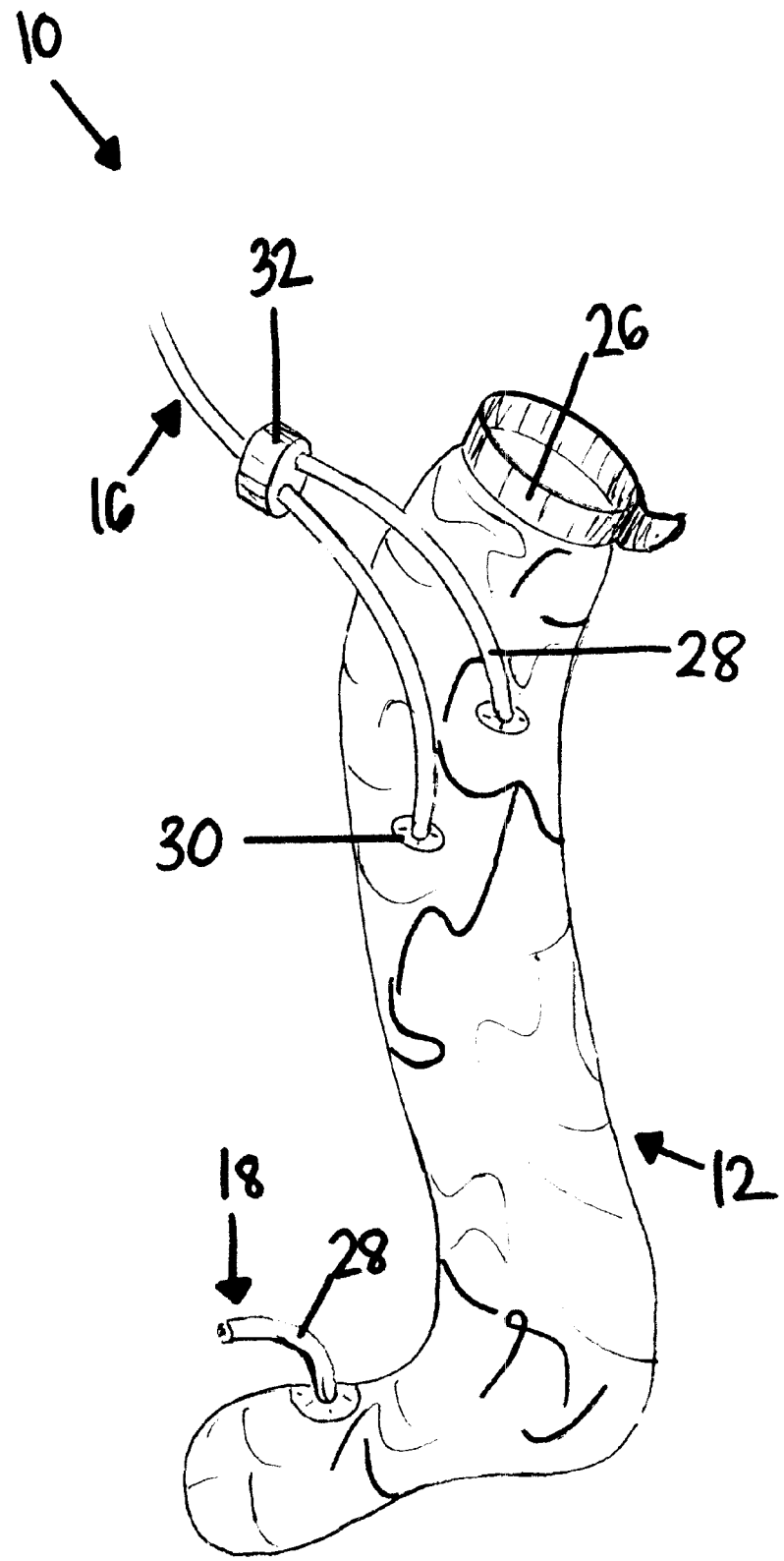

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

It will be understood that like or analogous elements and/or components, referred to herein, are identified throughout the drawings by like reference characters.

Referring now to the drawings, and to FIG. 1A in particular, a perspective schematic representation of medical dressing 10 is shown, which generally comprises means 12 for isolating an affected area of a patient, such as a burn, incision, abrasion, skin graft, and/or other abnormality, from an external environment, wherein placement of isolation means 12 defines a volume 14 (FIG. 1B) surrounding at least a portion of an affected area of a patient, means 16 for controllably inputting matter into the volume; and means 18 for controllably exhausting matter from the volume. It will be understood that FIG. 1A is merely a schematic representation of medical dressing assembly 10. As such, some of the components have been distorted from their actual scale for pictorial clarity.

For purposes of the present disclosure, isolation means 12 of medical dressing assembly 10 may include a patient engaging base member 20 and a cover member 22 hermetically associated therewith. Preferably patient engaging base member 20 includes an inner peripheral geometry greater than the affected area of the patient. As is further shown in FIG. 1A, the underside of patient engaging base member 20 may be at least partially associated with adhesive 24. Although not necessary, adhesive 24 is preferably fabricated from a hypoallergenic material so as to minimize any irritation surrounding the affected area of the patient. In addition, adhesive 24 may be covered, in whole or in part, with a protective, peel-away member 25 (FIG. 1B)—similar to those associated with the backing of a conventional band-aid. It will be understood that patient engaging base member is preferably fabricated from a conformable material such as a natural and synthetic polymeric resins and/or composites which are well known in the art. While preferred fabrication materials have been disclosed, for illustrative purposes only, numerous other materials are likewise contemplated for use including metals, ceramics, as well as commercially available double sided tape.

For purposes of the present disclosure, cover member 22 is expandable, which as will be discussed in greater detail below, enables volume 14 to vary depending upon, among other things, this thickness of cover member 22 as well as internal pressure within volume 14. Alternatively, cover member 22 may be fabricated from a non-expandable material, which enables volume 14 to remain constant during treatment of the affected area. Cover member 22 is preferably substantially transparent so as to enable observation of the affected area of the patient. Additionally, it is desirous for volume 14 to be pressurizable from approximately ambient pressure to approximately 10 pounds per square inch. Such pressurization can substantially preclude the patient from becoming dehydrated—especially when the affected area of the patient is rather large where discharge matter and fluid loss can rapidly occur. While a preferred pressure range has been disclosed, for illustrative purposes only, it will be understood that such a requisite pressure will vary from injury to injury, and that the only limitation relative to pressurizing volume 14 is that the pressure must be substantial enough to reduce dehydration of the affected area, and, in turn, the patient. Cover member 22 may be fabricated from any one of a number of materials, however, expandable latex type materials are preferred.

Figure 2I:
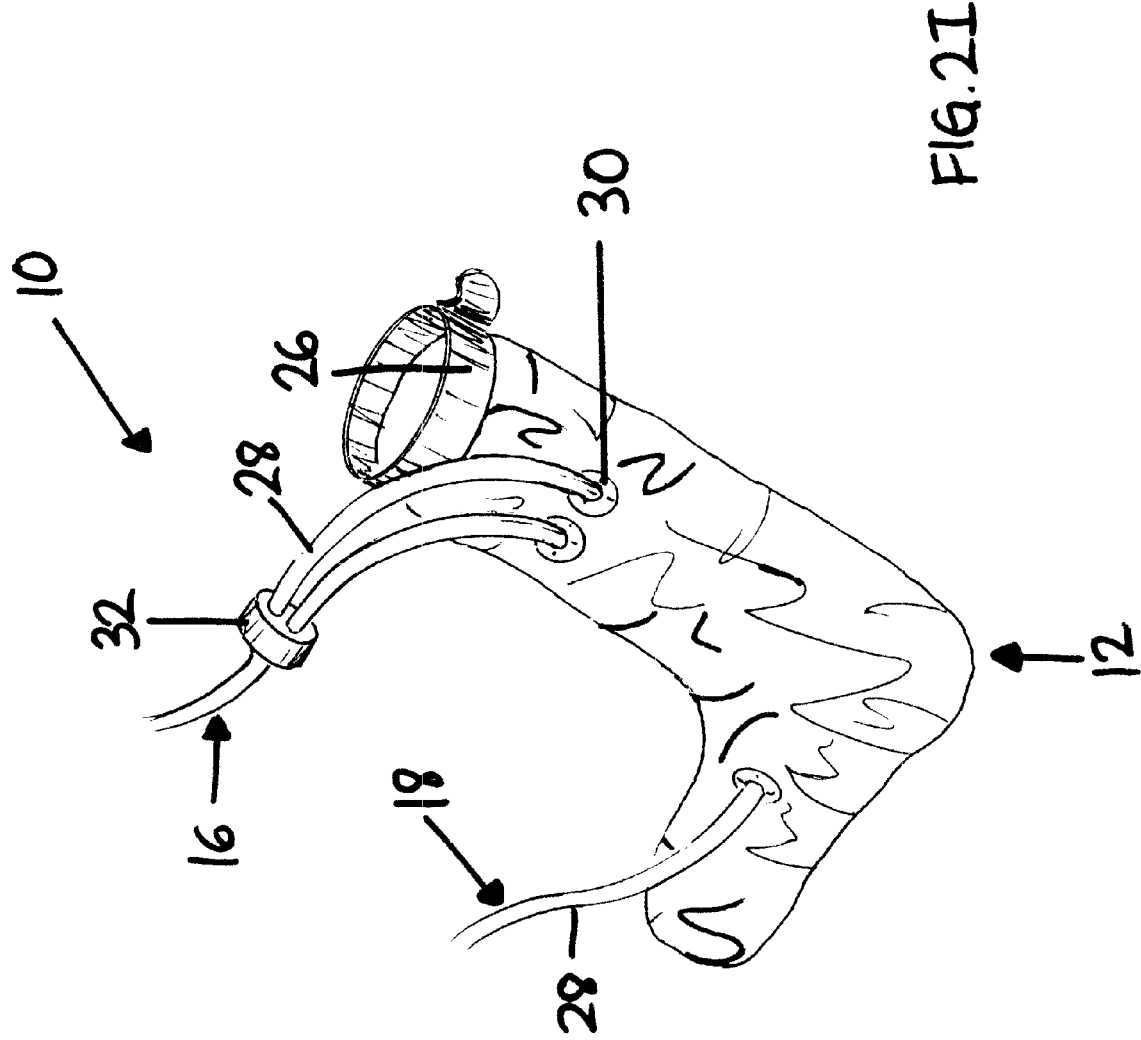

As is best shown in FIGS. 2A–2I, medical dressing assembly 10, may be configured into any one of a number of geometric configurations including those conforming to, for example, a hand dressing (FIG. 2A), a forearm dressing (FIG. 2B), an upper arm dressing (FIG. 2C), a facial dressing (FIG. 2D), an upper torso dressing (FIG. 2E), a lower torso dressing (FIG. 2F), an upper leg dressing (FIG. 2G), a lower leg dressing (FIG. 2H), a foot and ankle dressing (FIG. 2I). In such embodiments, medical dressing assembly 10 may include one or more patient engaging strap member(s) 26.

Patient engaging strap members 26 serve to effectively seal off the affected area of a patient from the external environment, and may be fabricated from any one of a number of materials including, natural and synthetic polymeric resins and/or composites. Preferably patient engaging strap member 26 is adjustable for adaptation to numerous different sized patients. Although not necessary, either one or both of the top surface or bottom surface of patient engaging strap member 26 can be at least partially coated with an adhesive, which may or may not be hypoallergenic. Similarly to the underside of patient engaging base member 20 of FIG. 1A, the underside of patient engaging strap member 26 may also include an adhesive covered with a protective, peel-away member. Alternatively, patient engaging strap member 26 may include a tie-securing mechanism and/or hook and loop securing mechanism, such as VELCRO—which is commercially available from numerous sources.

As is best shown in FIG. 1A and FIGS. 2A–2I, matter inputting means 16 may comprise one or more conduit(s) 28. Conduits 28 are preferably hermetically associated with isolation means 12, and in particular, at least one of patient engaging base member 20, patient engaging strap member 26, and/or cover member 22. Conduits 28 are preferably directly connected to isolation means 12 by connectors 30. Connectors 30 may comprise any one of a number of configurations that would be known to one having ordinary skill in the art—so long as the particular connector is capable of forming a substantially hermetic seal. It will be understood that while connectors 30 have been shown in particular locations, numerous other locations are contemplated in accordance with the present invention. It will be further understood that conduits 28 may be configured with various internal and/or external diameters.

In accordance with the present invention, and as is best shown in FIG. 1A, matter input means 16 can be routed from a single input to multiple inputs by a splitter 32, which allows matter to be introduced into volume 14 at multiple predetermined locations.

Figure 3:
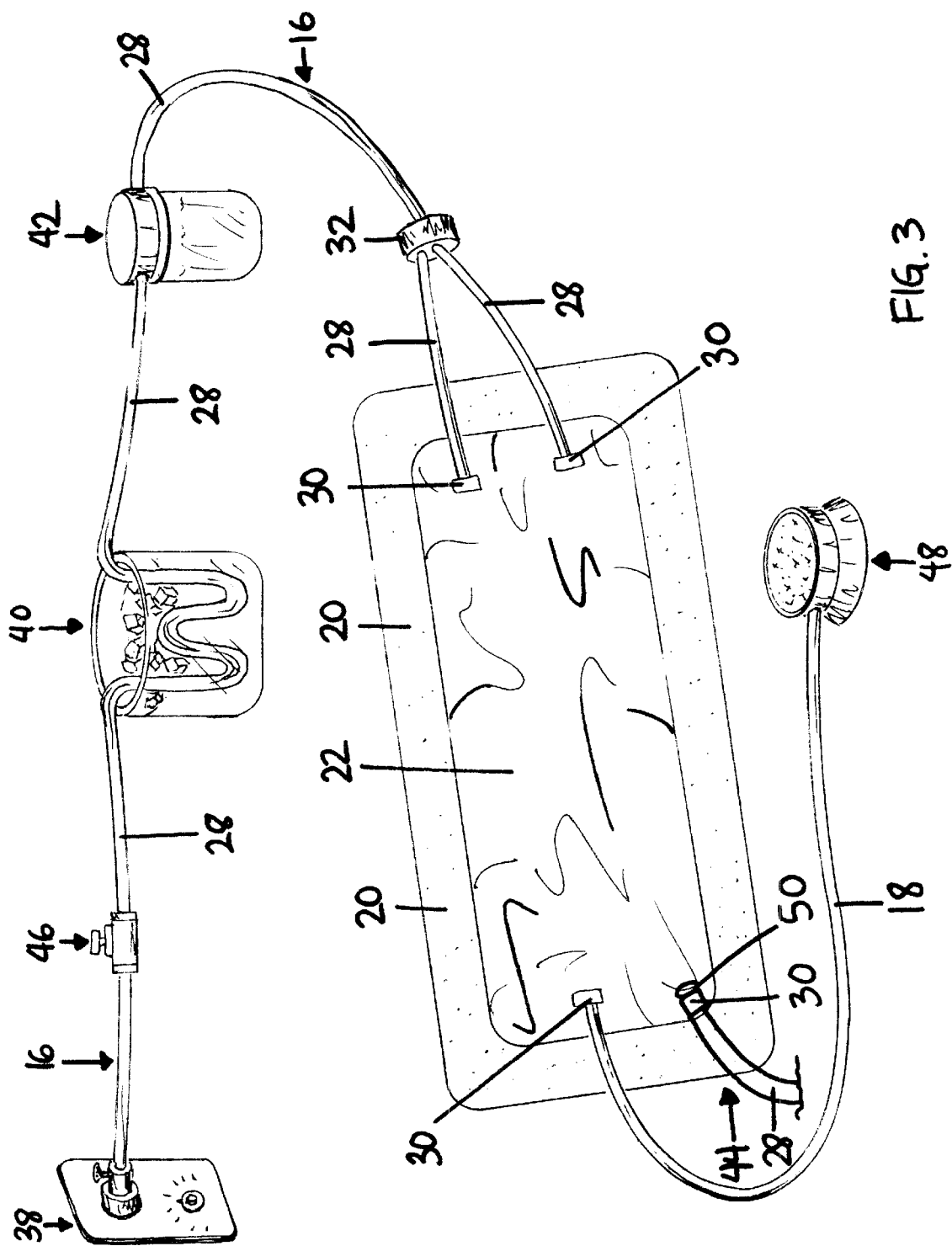
FIG. 3 of the drawings is a perspective view of a medical dressing assembly in accordance with the present invention.

As is shown in FIG. 3, matter input means 16 may be associated with one or more matter input rate regulating means 46, such as, for example, a pressure regulator, a clamp for pinching or narrowing associated conduit 28, or a filter which, in addition to removing undesired matter from matter input means 16, can optionally serve as a mechanism for regulating the matter input rate depending upon, among other things, the thickness and porosity of the filter.

As is best shown in FIG. 1A and FIGS. 2A–2I, matter exhaust means 18 may comprises one or more conduit(s) 28. Similar to matter input means 16, one or more conduit(s) 28 are preferably hermetically associated with isolation means 12, and in particular, at least one of patient engaging base member 20, patient engaging strap member 26, and/or cover member 22. Conduits 28 are preferably directly connected to isolation means 12 by connector 30. Connector 30 may comprise any one of a number of configurations that would be known to one having ordinary skill in the art—so long as the particular connector is capable of forming a substantially hermetic seal. While matter exhausting means 18 has been disclosed, for illustrative purposes only, as comprising one or more conduits 28, it will be understood that matter exhausting means 18 may also, or, alternatively comprise one or more apertures associated with isolation means 12 of a predetermined size.

Referring again to FIG. 3, matter exhaust means 18 may be associated with one or more matter exhaust rate regulating means 48, such as, for example, a pressure regulator, a clamp for pinching or narrowing associated conduit 28, or a filter which, in addition to removing undesired matter from matter exhaust means 18, can optionally serve as a mechanism for regulating the matter exhaust rate depending upon, among other things, the thickness and porosity of the filter.

As is shown in FIG. 3, medical dressing assembly 10 preferably comprises a source 38 for supplying a controlled gas. It will be understood that the particular controlled gas used in association with medical assembly 10 will vary from application to application, however, preferred controlled gas sources include air, purified air, a noble or inert gas, an oxygen enriched gaseous mixture, oxygen, and mixtures thereof.

Referring again to FIG. 3, medical dressing assembly 10 may optionally be associated with means 40 for cooling matter inputting means 16. Such cooling means may include, for example, a container filled with ice, ice water, water or other cold matter, upon which matter inputting means 16 can be dipped or otherwise associated with. In addition, other cooling means are contemplated for use in association with the present invention, including refrigerated containers. Of course, the type of cooling means will varying depending upon the particular situation. For example, a patient confined in a hospital type setting may be afforded a controlled, refrigerated container, while a field patient, such as a soldier, may be merely afforded crushable cold packs which are placed around matter input means 16.

As is also shown in FIG. 3, medical dressing assembly 10 may optionally comprise medication delivery means 42, such as a vaporizer or a nebulizer associated with matter inputting means 16. Such a feature is highly desirous inasmuch as most medications are administered in large quantities via oral introduction or intravenous introduction. In accordance with the present invention, medicine can be vaporized and/or nebulized and subsequently introduced into matter input means 16, which is directly, topically applied to the affected area in a substantially lower concentration that the conventional, above-identified medication administration means. Using such an embodiment enables a patient to receive only as much medication as is necessary to treat the affected area, which can substantially prolong, or, in some cases, eliminate the time period before the patient builds up a resistance to the medication. In addition, because the concentration of the drug can be substantially reduced, many adverse side effects associated with powerful healing and/or pain relieving medications can be minimized or, alternatively, outright eliminated. To be sure, such an improvement in medication administration to affected areas has enormous beneficial consequences.

In a preferred embodiment, and as is shown in FIG. 3, medical dressing assembly 10 may optionally comprise means 44 for collecting discharge matter from the affected area of a patient. Discharge collection means 44 preferably functions as a gravity drain through an aperture 50 associated with isolation means 12. Conduit 28 is preferably attached to aperture 50 through connector 30, which assists in directing discharge matter to a predetermined location. Although not shown, discharge collection means 44 can also be associated with a suction mechanism to expedite removal of unwanted discharge from the affected area.

In operation, medical dressing assembly 10, which includes an isolating member having at least one patient engaging member and a cover member associated therewith, at least one input conduit, and an exhaust is placed on the patient, thereby operatively securing the isolating member onto the patient so that at least a portion of an affected area of a patient is isolated from an external environment. Second, matter such as a controlled gas and/or medication is supplied into the medical dressing assembly through the at least one input conduit, which builds pressure within volume 14 (FIG. 1B). Third matter retained within volume 14 is exhausted into the external environment. It will be understood that the rate of exhaust is preferably configured to be less than the input rate of matter so that the system maintains a positive internal pressure to substantially preclude matter from the external environment from entering volume 14, and, in turn, the affected area of the patient.

Preferably the above-identified method further comprises at least one of the following steps: cooling the matter prior to the step of supplying matter into the medical dressing assembly, and introducing vaporized or nebulized medication into the medical dressing assembly through the matter input means, and, in turn, applying the medication to the localized, affected area of the patient.

Although not necessary, the step of venting matter from the exhaust into the external environment may include the step of filtering the matter prior to venting the exhaust into the external environment.

Using medical dressing assembly 10 avails the patient having an affected area numerous benefits including: (1) the isolation means substantially precludes matter from the external environment from contacting the affected area of the patient; (2) the controlled input of matter, such as oxygen, can substantially eliminate the residual "burning sensation" felt by burn patients; (3) the dressing assembly does not directly contact the affected area thereby further mitigating pain associated with the affected area relative to conventional medical dressings; (4) the pressure within the volume of the medical dressing assembly substantially precludes fluid loss and the complications associated with dehydration; (5) the affected area is readily observable, thereby enabling a physician or care taker to examiner the affected area without disturbing the medical dressing assembly; (6) the matter input means generates a flow of gas, thereby properly circulating the affected area and reducing both pain as well as the associated healing time and; (7) the application of medication is topically localized, which substantially reduces the concentration of the medication, thereby prolonging associated resistances as well as minimizing any adverse side effects. In addition, under certain circumstances, the concentration of the medication may be low enough so that a patient that would otherwise have an adverse allergic reaction can be administered a particular medication.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A medical dressing assembly, comprising:
   means for isolating an affected area of a patient from an external environment including:
   at least one patient engaging strap member, the at least one patient engaging strap member having a bottom surface positionable so as to be substantially internally facing; and
   a cover member extending away from the at least one patient engaging strap member, the cover member defining a volume, the at least one patient engaging strap member providing access to the volume,
   wherein the bottom surface of the at least one patient engaging strap member is capable of engaging a portion of the patient, to, in turn, substantially confine at least a portion of the affected area of a patient within the volume defined by the cover member;
   means for controllably inputting matter into said volume; and
   means for controllably exhausting matter from said volume.

2. The medical dressing assembly according to claim 1, wherein said isolation means is geometrically configurable into at least one of the group consisting of a hand dressing, a forearm dressing, an upper arm dressing, a facial dressing, an upper torso dressing, a lower torso dressing, an upper leg dressing, a lower leg dressing, a foot and ankle dressing, and mixtures thereof.

3. The medical dressing assembly according to claim 1, wherein said patient engaging strap member includes means for adjusting the circumference of the internally facing bottom surface.

4. The medical dressing assembly according to claim 3, wherein said patient engaging strap member includes an adhesive positioned along at least a portion of the internally facing bottom surface.

5. The medical dressing assembly according to claim 4, wherein said adhesive is covered with a protective, peel-away member.

6. The medical dressing assembly according to claim 1, wherein said cover member comprises a flexible material to, in turn, facilitate a variation of the volume of the cover member.

7. The medical dressing assembly according to claim 6, wherein said cover member is substantially transparent, thereby enabling observation of said affected area of said patient.

8. The medical dressing assembly according to claim 1, wherein said cover member comprises a substantially rigid material, thereby defining a substantially fixed volume.

9. The medical dressing assembly according to claim 8, wherein said cover member is substantially transparent, thereby enabling observation of said affected area of said patient.

10. The medical dressing assembly according to claim 1, wherein said matter inputting means comprises at least one conduit hermetically associated with said isolation means.

11. The medical dressing assembly according to claim 1, wherein said matter inputting means comprises two conduits hermetically associated with said isolation means.

12. The medical dressing assembly according to claim 1, wherein said matter inputting means is associated with at least one of a regulator, a clamp, and a filter for controlling the input rate of matter into said volume.

13. The medical dressing assembly according to claim 1, wherein said matter exhausting means comprises at least one aperture associated with said isolation means.

14. The medical dressing assembly according to claim 1, wherein said matter exhausting means comprises at least one conduit hermetically associated with said isolation means.

15. The medical dressing assembly according to claim 1, wherein said matter exhausting means is associated with at least one of a regulator, a clamp, and a filter for controlling the exhaust rate of matter out of said volume.

16. The medical dressing assembly according to claim 1, further comprising a source for supplying a controlled gas, the controlled gas supplying source positioned in fluid communication with the controllable matter inputting means, to, in turn, supply a controlled gas to the volume.

17. The medical dressing assembly according to claim 16, wherein said controlled gas is selected from the group consisting of air, purified air, a noble or inert gas, an oxygen enriched gaseous mixture, oxygen, and mixtures thereof.

18. The medical dressing assembly according to claim 1, further comprising cooling means positioned proximate to said matter inputting means, the cooling means structurally configured to decrease the temperature of the matter inputting means and matter extending therethrough.

19. The medical dressing assembly according to claim 1, further comprising at least one of a vaporizer or nebulizer positioned in fluid communication with said matter inputting means.

20. The medical dressing assembly according to claim 1, further comprising filtering means positioned in fluid communication with said matter exhausting means.

21. The medical dressing assembly according to claim 1, further comprising means for collecting discharge matter from said affected area.

22. The medical dressing assembly according to claim 1, wherein the controllable matter inputting means and the controllable matter exhausting means are configured so as to maintain the volume at a greater pressure than ambient.

23. The medical dressing assembly according to claim 22, wherein the controllable matter inputting means and the controllable matter exhausting means are configured so as to maintain a relative pressure difference between ambient and the volume of at least about 10 pounds per square inch.

24. The medical dressing assembly according to claim 1 wherein the at least one patient engaging strap member further comprises a plurality of patient engaging strap members, each patient engaging strap member having a bottom surface positionable so as to be substantially internally facing.

25. The medical dressing assembly according to claim 1 wherein the at least one patient engaging strap member further comprises at least four patient engaging strap members, each patient engaging strap member having a bottom surface positionable so as to be substantially internally facing.

26. The medical dressing assembly according to claim 1 wherein the matter comprises at least one of a gas and a liquid.

27. A method of dressing an affected area of a patient, comprising the steps of:
   providing a medical dressing assembly including; an isolating member having at least one patient engaging member and a cover member associated therewith; at least one input conduit; and an exhaust;
   operatively securing said isolating member associated with said cover member onto said patient so that at least a portion of said affected area of said patient is isolated from an external environment;
   supplying matter into said medical dressing assembly through said at least one input conduit;
   venting matter from said exhaust into an external environment; and
   controlling at least one of the supplying of matter and the venting of matter, to, in turn, maintain a relative pressure difference between ambient and said medical dressing assembly due to the supply of matter into said medical dressing assembly.

28. The method according to claim 27, wherein the step of operatively securing said isolating member onto said patient includes the step of substantially precluding airborne matter from the external environment from contacting said affected area of said patient.

29. The method according to claim 27, wherein the step of supplying matter into said medical dressing assembly through said at least one input conduit includes the step of pressurizing a volume surrounding said affected area of said patient.

30. A method of dressing an affected area of a patient, comprising the steps of:
   providing a medical dressing assembly including; an isolating member having at least one patient engaging member and a cover member associated therewith; at least one input conduit; and an exhaust;
   operatively securing said isolating member associated with said cover member onto said patient so that at least a portion of said affected area of said patient is isolated from an external environment;
   cooling matter for the supply thereof into said medical dressing assembly;
   supplying said matter into said medical dressing assembly through said at least one input conduit; and
   venting matter from said exhaust into an external environment.

31. A method of dressing an affected area of a patient, comprising the steps of:
   providing a medical dressing assembly including; an isolating member having at least one patient engaging member and a cover member associated therewith; at least one input conduit; and an exhaust;
   operatively securing said isolating member associated with said cover member onto said patient so that at least a portion of said affected area of said patient is isolated from an external environment;
   supplying matter into said medical dressing assembly through said at least one input conduit;
   introducing vaporized or nebulized medication into said medical dressing assembly through said at least one input conduit, and, in turn, applying said medication to said localized area of said patient; and
   venting matter from said exhaust into an external environment.

32. A method of dressing an affected area of a patient, comprising the steps of:
   providing a medical dressing assembly including; an isolating member having at least one patient engaging member and a cover member associated therewith; at least one input conduit; and an exhaust;
   operatively securing said isolating member associated with said cover member onto said patient so that at least a portion of said affected area of said patient is isolated from an external environment;
   supplying matter into said medical dressing assembly through said at least one input conduit;
   filtering said matter after supply thereof into said medical dressing assembly; and
   venting matter from said exhaust into an external environment.

* * * * *